US006619295B1

(12) United States Patent
Okabe et al.

(10) Patent No.: US 6,619,295 B1
(45) Date of Patent: Sep. 16, 2003

(54) HAIR COSMETIC COMPOSITION

(75) Inventors: Hiroko Okabe, Tokyo (JP); Yutaka Shibata, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/699,482

(22) Filed: Oct. 31, 2000

(51) Int. Cl.$^7$ ............................ A61K 7/06; A61K 7/08
(52) U.S. Cl. ..................... 132/202; 134/42; 510/123; 510/504; 510/505; 424/70.19; 424/70.27; 424/70.28
(58) Field of Search .............................. 8/405, 406, 410, 8/411; 132/202; 134/42; 510/123, 505, 504; 424/70.19, 70.27, 70.28

(56) References Cited

U.S. PATENT DOCUMENTS

| | | | | |
|---|---|---|---|---|
| 4,459,285 A | * | 7/1984 | Grollier et al. | 424/74 |
| 5,254,333 A | * | 10/1993 | Kajino et al. | 424/70 |
| 5,651,960 A | * | 7/1997 | Chan et al. | 424/70.6 |

FOREIGN PATENT DOCUMENTS

| | | | | |
|---|---|---|---|---|
| JP | 4-356413 | | 12/1992 | |
| JP | 4656413 | * | 12/1992 | A61K/3/13 |
| JP | 406271423 A | * | 9/1994 | A61K/7/02 |
| JP | 7-69837 | | 3/1995 | |
| JP | 7-309724 | | 11/1995 | |
| JP | 8-048611 | | 2/1996 | |
| JP | 08-048611 | * | 2/1996 | A61K/7/13 |
| JP | 11-302130 | | 11/1999 | |

* cited by examiner

Primary Examiner—Yogendra N. Gupta
Assistant Examiner—Eisa Elhilo
(74) Attorney, Agent, or Firm—Oblon, Spivak, McClelland, Maier & Neustadt, P.C.

(57) ABSTRACT

A hair cosmetic composition containing (A) a cationic surfactant; (B) one or more organic solvents selected from among an N-alkylpyrrolidone, a lower alkylene carbonate, and an aromatic alcohol; (C) a lower alcohol or a lower polyol; and (D) an alkaline ingredient. The composition efficiently removes an acid hair-dye composition from the hair without causing any damage to the hair.

14 Claims, No Drawings

HAIR COSMETIC COMPOSITION

TECHNICAL FIELD

The present invention relates to a hair cosmetic composition for removing an acid hair-dye composition from the hair.

BACKGROUND ART

Conventionally, in order to remove a hair dye composition from the hair, bleaching agents have been employed. However, bleaching agents damage the hair, and involve some further drawbacks; i.e., the agents decompose melanin contained in the hair, and make the hair color bright. In order to improve the removal of such a hair dye composition, a dye-removing composition containing a sulfite salt has been proposed (Japanese Patent Application Laid-Open (kokal) No. 4-356413). However, this composition does not remove the hair-dye composition satisfactorily, and also damages the hair.

For removing a hair dye composition adhering to the skin, a dye-removing composition containing a cation surfactant, benzyloxyethanol, and a C2–C4 lower alcohol has been proposed (Japanese Patent Application Laid-Open (kokai) No. 8-48611).

However, when the dye-removing composition is employed, although hair dye compositions adhering to the skin can be removed, the dye compositions cannot be efficiently removed from the hair.

In view of the foregoing, an object of the present invention is to provide a hair cosmetic composition which does not damage the hair, and facilitates removal of an acid hair-dye composition.

DISCLOSURE OF THE INVENTION

The present inventors have found that a dye-removing composition employed for removing an acid hair-dye composition adhering to the skin affects the hair differently than it affects the skin, and thus the hair-dye composition cannot be removed from the hair by use of the dye-removing composition; and that, when a dye-removing composition containing an alkaline ingredient is applied to the hair, the acid hair-dye composition can be efficiently removed from the hair, and the dye-removing composition does not damage the hair. The present invention has been accomplished on the basis of these findings.

Accordingly, the present invention provides an alkaline hair cosmetic composition comprising the following ingredients (A), (B), (C), and (D):

(A) a cationic surfactant;
(B) one or more organic solvents selected from among an N-alkylpyrrolidone, a lower alkylene carbonate, and an aromatic alcohol;
(C) a lower alcohol or a lower polyol; and
(D) an alkaline ingredient.

The present invention also provides a method for removing a hair dye composition from the hair, which comprises applying the hair cosmetic composition to hair which has been dyed with a hair dye composition; and subsequently rinsing the hair.

Best Mode for Carrying Out the Invention

Examples of ingredient (A), which is a cationic surfactant employed in the present invention, include compounds represented by the following formula (1) or (2):

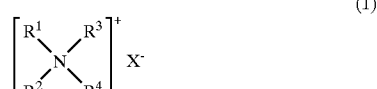

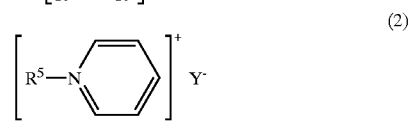

(in formula (1), at least one of $R^1$, $R^2$, $R^3$, and $R^4$ represents a linear or branched C8–C36 alkyl group or hydroxyalkyl group, or a benzyl group, each of the remaining of these represents a C1–C3 alkyl group or hydroxyalkyl group, and X represents a halogen atom or a C1–C2 alkylsulfuric group; and in formula (2), $R^5$ represents a linear or branched C8–C36 alkyl group, and Y represents a halogen atom.)

In formulas (1) and (2), a C8–C36 alkyl group or hydroxyalkyl group represented by $R^1$ through $R^5$ is preferably a C10–C36 alkyl group or a hydroxyalkyl group.

Specific examples of ingredient (A) include lauryltrimethylammonium chloride, cetyltrimethylammonium chloride, cetyltrimethylammonium bromide, stearyltrimethylammonium chloride, behenyltrimethylammonium chloride, stearyltrimethylammonium bromide, lauryltrimethylammonium bromide, behenyltrimethylammonium chloride, isostearyltrimethylammonium chloride, dicetyldimethylammonium chloride, distearyldimethylammonium chloride, dicocoyldimethylammonium chloride, myristyldimethylbenzylammonium chloride, stearyldimethylbenzylammonium chloride, laurylpyridinium chloride, cetylpyridinium chloride, and benzalkonium chloride.

Ingredient (A) is preferably lauryltrimethylammonium chloride, cetyltrimethylammonium chloride, stearyltrimethylammonium chloride, behenyltrimethylammonium chloride, or distearyldimethylammonium chloride. Of these, behenyltrimethylammonium chloride is more preferable.

One or more cationic surfactants may be employed as ingredient (A). In order to satisfactorily remove a hair dye composition, ingredient (A) is preferably incorporated in an amount of 0.05–10 wt. %, more preferably 0.1–5 wt. %, on the basis of the entirety of the hair cosmetic composition.

Ingredient (B), which is an organic solvent employed in the present invention, is selected from among N-alkylpyrrolidone, lower alkylene cartbonate, and aromatic alcohol. Examples of N-alkylpyrrolidone include N-methylpyrrolidone and N-ethylpyrrolidone: examples of lower alkylene carbonate include ethylene carbonate and propylene carbonate; and examples of aromatic alcohol include benzyl alcohol, benzyloxyethanol, and β-phenylethyl alcohol.

Ingredient (B) is preferably N-methylpyrrolidone, benzyl alcohol, or benzyloxyethanol. Of these, benzyl alcohol or benzyloxyethanol is more preferable.

One or more organic solvents may be employed as ingredient (B). In order to satisfactorily remove a hair dye composition, ingredient (B) is preferably incorporated in an amount of 0.1–40 wt. %, more preferably 1–30 wt. %, much more preferably 5–20 wt. %, on the basis of the entirety of the hair cosmetic composition.

Ingredient (C) employed in the present invention is one or more species selected from among lower alcohols and lower polyols. Preferably, C2–C6 lower alcohols or lower polyols are employed. Specific examples include ethanol, isopropanol, n-propanol, n-butanol, ethylene glycol, propylene glycol, isoprene glycol, hexylene glycol, 1,3-butylene glycol, glycerin, and diglycerin.

Ingredient (C) is more preferably ethanol, isopropanol, or 1,3-butylene glycol. When a water-soluble polymer is employed as ingredient (E); i.e., a thickener, ethanol and 1,3-butylene glycol are preferably employed in combination in order to disperse the water-soluble polymer in the hair cosmetic composition.

Ingredient (C) is preferably incorporated in an amount of 0.1–50 wt. %, more preferably 5–30 wt. %, on the basis of the entirety of the hair cosmetic composition.

Examples of ingredient (D); i.e., an alkaline ingredient employed in the present invention, include strong aqueous ammonia; monoethanolamine; diethanolamine; triethanolamine; isopropanolamine; diisopropanolamine; triisopropanolamine; 2-amino-2-methyl-1-propanol; sodium carbonate; sodium hydrogencarbonate; hydroxides of alkali metal, such as sodium hydroxide and potassium hydroxide; and fatty acid salts, such as sodium oleate, sodium stearate, and triethanolamine stearate.

In order to facilitate removal of a hair dye composition, ingredient (D) is more preferably triethanolamine or monoethanolamine.

One or more alkaline ingredients may be employed as ingredient (D). Ingredient (D) is preferably incorporated in an amount of 0.01–10 wt. %, more preferably 0.1–5 wt. %, much more preferably 0.5–2.5 wt. %, on the basis of the entirety of the hair cosmetic composition. This is because, when the composition contains ingredient (D) in such an amount, even if the composition adheres to the skin, the composition does not irritate the skin.

When the hair cosmetic composition of the present invention contains a thickener (ingredient (E).) in addition to the aforementioned ingredients, the composition becomes easy to handle, and enables removal of a dye from a portion of dyed hair; e.g., from some strands of dyed hair. Furthermore, application of the composition to unnecessary portions (e.g., the scalp) may be prevented, and running of the composition into the eyes or to the forehead or the ears is prevented. In addition, when ingredient (E) is employed in combination with a specific cationic surfactant (ingredient (A)), damage of the composition to the skin can be reduced. Ingredient (E) is preferably a water-soluble polymer, more preferably a nonionic water-soluble polymer such as hydroxyethyl cellulose or hydroxypropylmethyl cellulose, or a cationic water-soluble polymer such as cationized cellulose.

Ingredient (E) may be a combination of two or more species. In order to improve handling of the hair cosmetic composition, and to reduce damage of the composition to the skin, ingredient (E) is preferably incorporated in an amount of 0.1–20 wt. %, more preferably 0.5–10 wt. %, much more preferably 0.8–5 wt. %, on the basis of the entirety of the composition.

The hair cosmetic composition of the present invention may further contain appropriate amounts of widely-used cosmetic ingredients, such as nonionic surfactants, amphipathic surfactants, paraffin oils, lanoline, higher alcohols, oil agents such as silicone oil, bactericides, hair-growing and hair-nourishing agents, preservatives, anti-dandruff agents, and perfumes, so long as they do not impair the effect of the present invention.

The hair cosmetic composition of the present invention may be produced through a customary process. In order to facilitate removal of a dye, the composition preferably has a pH falling within an alkali region, more preferably a pH of 8–12, much more preferably a pH of 9–11.

The product form of the hair cosmetic composition of the present invention is not particularly limited, and the composition may assume any product form of liquid, emulsion, cream, gel, paste, aerosol, and aerosol foam. Of these, a form of emulsion, cream, gel, or paste is preferable, since a product of such a form is easy to use.

The hair cosmetic composition of the present invention is used, for example, as follows. An appropriate amount of the composition is applied to hair which has been dyed with an acid hair-dye composition. Subsequently, the hair is allowed to stand at preferably 10–50° C. for 3 to 30 minutes, and then the hair is rinsed.

EXAMPLES

The present invention will next be described in more detail by way of Examples.

Example 1

Hair cosmetic compositions containing ingredients in the compositional proportions shown in Table 1 were produced by means of a customary method. The respective compositions were evaluated in terms of extent of removal of an acid hair-dye composition, extent of bleaching of black hair, and extent of damage to the hair. The results are shown in Table 1.

(Evaluation Methods)

(1) Extent of removal of acid hair-dye composition

The hair cosmetic composition (1 g) was evenly applied to hair fibers (black human hair fibers and gray human hair fibers: each 1 g) which had been dyed with a commercially available acid hair-dye composition. Subsequently, the resultant hair fibers were allowed to stand at 40° C. for 15 minutes. Thereafter, the hair fibers were washed, and the effectiveness of removal of the acid hair-dye composition was evaluated on the basis of the following standards:

O: the hair-dye composition was effectively removed, and gray hair became fully visible;

Δ: the hair-dye composition was removed to some extent but some remained in the hair, and gray hair became slightly visible; and X: most of the hair-dye composition remained in the hair, and gray hair was almost invisible.

(2) Bleaching of black hair

Whether or not black hair was bleached through the procedure of (1) was evaluated on the basis of the following standards:

O: black hair was not bleached; and

X: black hair was bleached.

(3) Damage to the hair

The hair cosmetic composition (20 g) was evenly applied to hair fibers (black human hair fibers: 20 g), the resultant hair fibers were allowed to stand at 40° C. for 15 minutes, and then the hair fibers were washed. This procedure was carried out three times. Thereafter, the feel of the hair fibers was evaluated by 20 panelists on the basis of the following standards:

O: 60% or more of the panelists assessed that the feel of the above-treated hair fibers was similar to or better than that of non-treated hair fibers; and X: less than 60% of the panelists assessed that the feel of the above-treated hair fibers was worse than that of non-treated hair fibers.

TABLE 1

(wt. %)

| Ingredient | Composition of the present invention | | | Comparative composition | | | | | | |
|---|---|---|---|---|---|---|---|---|---|---|
| | 1 | 2 | 3 | 1 | 2 | 3 | 4 | 5 | 6 | 7 |
| Stearyltrimethyl-ammonium chloride | 2 | 2 | | 2 | | | 2 | 2 | 1.5 | Bleaching agent |
| Distearyldimethyl ammonium chloride | | | 2 | | 2 | | | | | |
| Benzyloxyethanol | 10 | | 5 | | 10 | 5 | 10 | 10 | 5 | |
| Benzyl alcohol | | 10 | | | | | | | | |
| 1,3-Butylene glycol | | | 5 | | | | | | | |
| Ethanol | 10 | 10 | | 10 | 10 | 10 | | 10 | 10 | |
| Monoethanolamine | 1 | 1 | 1 | 1 | 1 | | 1 | | | |
| Sodium sulfite | | | | | | | | 1.5 | | |
| Purified water | Balance | Balance | Balance | Balance | Balance | Balance | Balance | Balance | Balance | |
| Extent of removal of acid hair-dye composition | O | O | O | X | X | X | X | Δ | X | Δ |
| Bleaching of black hair | O | O | O | O | O | O | O | O | O | X |
| Damage to the hair | O | O | O | O | O | O | O | X | O | X |

Example 2

Hair cosmetic compositions containing ingredients in the compositional proportions shown in Table 2 were produced by means of a customary method. The respective compositions were evaluated in terms of extent of removal of an acid hair-dye composition, extent of damage to the hair, extent of damage to the skin, and degree of running. Some of the results are shown in Table 2.

(Evaluation Methods)

(1) Extent of removal of acid hair-dye composition The procedure of Example 1 was repeated, except that only gray human hair fibers dyed with an acid hair-dye composition were employed, to thereby evaluate the effect.

(2) Damage to the hair

The procedure of Example 1 was repeated, to thereby evaluate damage to the hair.

TABLE 2

(wt. %)

| Ingredient | Composition of the present invention | | |
|---|---|---|---|
| | 4 | 5 | 6 |
| Behenyltrimethylammonium chloride | 1 | 1.6 | 2 |
| Benzyloxyethanol | 10 | 15 | 8 |
| 1,3-Butylene glycol | | | 5 |
| Ethanol | 15 | 20 | 5 |
| Monoethanolamine | 1 | 1 | 1 |
| Hydroxyethyl cellulose | 1 | 0.5 | 1 |
| Hydroxypropylmethyl cellulose | | 1.5 | |
| Cationized cellulose | | | 0.2 |
| Purified water | Balance | Balance | Balance |

TABLE 2-continued (wt. %)

| Ingredient | Composition of the present invention | | |
|---|---|---|---|
| | 4 | 5 | 6 |
| Extent of removal of acid hair-dye composition | O | O | O |
| Damage to the hair | O | O | O |

(3) Damage to the Skin

The test employed 31 adult participants. The hair cosmetic composition was diluted tenfold with water, and the diluted composition was applied onto patches. Subsequently, one patch was applied to the skin on the back of each participant for 24 hours, and then removed. The skin was observed immediately after removal of the patch, 24 hours after removal of the patch, and 48 hours after removal of the patch. Damage to the skin was evaluated on the basis of the following scores:

4: blister formed;

3: papule formed;

2: erythema with edema occurred;
1: apparent erythema occurred; and
0: no damage.

The respective hair cosmetic compositions were evaluated three times on the 31 participants, and the average scores (highest possible score: 4) for the respective compositions were obtained.

The average score for Composition 5 of the present invention was found to be 0.61. The average score for a modified formulation of Composition 5, which was produced by replacing behenyltrimethylammonium chloride with cetyltrimethylammonium chloride, was 0.06.

(4) Degree of Running

The hair cosmetic composition was applied to the hair, and the degree of running of the composition to portions other than the hair (scalp, forehead, etc.) was obtained. Firstly, the hair cosmetic composition was applied to a wig (the head of a doll in which hair fibers had been inserted) such that 1 g of the composition was applied to 1 g of the hair fibers. Subsequently, the resultant hair fibers were allowed to stand for 15 minutes while the moisture content was maintained. Thereafter, the hair fibers onto which the composition had been applied were cut, the cut hair fibers were weighed, and then the degree (%) of running of the composition was calculated.

From the calculations, the degree of running of Compositions 4 through 6 of the present invention was found to be less than 1%. The degrees of running of these compositions not containing thickeners were also obtained. Briefly, Composition 4, which does not contain hydroxyethyl cellulose, Composition 5, which does not contain hydroxypropylmethyl cellulose, and Composition 6, which does not contain cationized cellulose, exhibited degrees of running of 8%, 9%, and 7%, respectively.

INDUSTRIAL APPLICABILITY

The hair cosmetic composition of the present invention does not damage hair, facilitates removal of an acid hair-dye composition from the hair, and does not bleach black hair.

What is claimed is:

1. A method for removing an acid hair dye composition from the hair, which comprises applying to hair, which has been dyed with a hair dye composition, an aqueous alkaline hair cosmetic composition, having a pH of 8–12, consisting of the following ingredients (A), (B), (C) and (D):
   (A) a cationic surfactant;
   (B) one or more organic solvents selected from the group consisting of N-alkylpyrrolidone, a lower alkylene carbonate, and an aromatic alcohol;
   (C) a lower alcohol or a lower polyol;
   (D) an alkaline ingredient; and
   subsequently rinsing the hair thereby removing hair dye by dissolution of the dye from the hair without bleaching the hair which decomposes melanin contained in the hair.

2. The method of claim 1, wherein said aromatic alcohol (B) is β-phenylethyl alcohol, benzyloxyethanol or benzyl alcohol.

3. The method of claim 1, wherein said lower alcohol is ethanol, isopropanol, n-propanol or n-butanol.

4. The method of claim 1, wherein said lower polyol is ethylene glycol, propylene glycol, isoprene glycol, hexylene glycol, 1,3-butylene glycol, glycerin or diglycerin.

5. The method of claim 1, wherein said cationic surfactant is lauryltrimethylammonium chloride, cetyltrimethylammonium chloride, cetyltrimethylammonium bromide, stearyltrimethylammonium chloride, behenyltrimethylammonium chloride, stearyltrimethylammonium bromide, lauryltrimethylammonium bromide, behenyltrimethylammonium chloride, isostearyltrimethylammonium chloride, dicetyldimethylammonium chloride, distearyldimethylammonium chloride, dicocoyldimethylammonium chloride, myristyldimethylbenzylammonium chloride, stearyldimethylbenzylammonium chloride, laurylpyridinium chloride, cetylpyridinium chloride and benzalkonium chloride.

6. The method of claim 1, wherein the content of organic solvent component (B) ranges from 0.1–40 wt. %, based on the weight of the cosmetic hair composition.

7. The method of claim 1, wherein the amount of cationic surfactant (A) in the composition ranges from 0.05 to 10 wt. % based on the weight of the hair cosmetic composition.

8. The method of claim 1, wherein component (C) is a $C_{2-6}$-alcohol or a $C_{2-6}$-polyol.

9. The method according to claim 1, wherein said ingredient (A) is a cationic surfactant represented by the following formula (1) or (2):

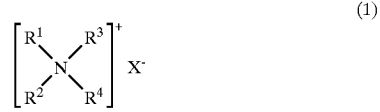

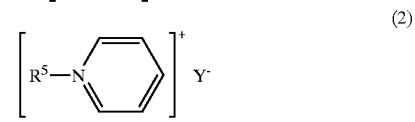

in formula (1), at least one of $R^1$, $R^2$, $R^3$, and $R^4$ represents a linear or branched $C_8$–$C_{36}$-alkyl group or hydroxyalkyl group, or a benzyl group, each of the remaining of these represents a $C_1$–$C_3$-alkyl group or hydroxyalkyl group, and X represents a halogen atom or a $C_1$–$C_2$-alkylsulfuric group; and in formula (2), $R^5$ represents a linear or branched $C_8$–$C_{36}$-alkyl group, and Y represents a halogen atom.

10. A method for removing an acid hair dye composition from the hair, which comprises applying to hair, which has been dyed with a hair dye composition, an aqueous alkaline hair cosmetic composition, with a pH of 8–12, consisting of the following ingredients (A), (B), (C), (D) and (E):
    (A) from 0.05–10 wt % of a cationic surfactant;
    (B) from 0.1–40 wt % of one or more organic solvents selected from the group consisting of an N-alkylpyrrolidone, a lower alkylene carbonate and an aromatic alcohol;
    (C) from 0.1–50 wt % of a lower alcohol or a lower polyol;
    (D) from 0.01–10 wt % of an alkaline ingredient;
    (E) from 0.1–20 wt % of a thickener; and
    subsequently rinsing the hair thereby removing hair dye by dissolution of the dye from the hair without bleaching the hair which decomposes melanin contained in the hair.

11. The method according to claim 10, wherein the thickener is a non-ionic water-soluble polymer or a cationic water soluble polymer.

12. The method according to claim 11, wherein the non-ionic water-soluble polymer is hydroxyethyl cellulose or hydroxypropylmethyl cellulose and said cationic water soluble polymer is cationized cellulose.

13. A method for removing an acid hair dye composition from the hair, which comprises applying to hair, which has been dyed with a hair dye composition, an aqueous alkaline hair cosmetic composition, having a pH of 8–12, consisting of the following ingredients (A), (B), (C), (D) and (F):

(A) a cationic surfactant;

(B) one or more organic solvents selected from the group consisting of N-alkylpyrrolidone, a lower alkylene carbonate, and an aromatic alcohol;

(C) a lower alcohol or a lower polyol;

(D) an alkaline ingredient; and (F) at least one cosmetic ingredient selected from the group consisting of nonionic surfactants, amphiphatic ingredients, paraffin oils, lanoline, higher alcohols, silicone oils, bactericides, hair-growing and hair-nourishing agents, preservatives, antidandruff agents, aerosolizing agent and perfumes, and subsequently rinsing the hair thereby removing hair dye by dissolution of the dye from the hair without bleaching the hair which decomposes melanin contained in the hair.

14. A method for removing an acid hair dye composition from the hair, which comprises applying to hair, which has been dyed with a hair dye composition, an aqueous alkaline hair cosmetic composition, with a pH of 8–12, consisting of the following ingredients (A), (B), (C), (D), (E) and (F).

(A) from 0.05–10 wt % of a cationic surfactant;

(B) from 0.1–40 wt % of one or more organic solvents selected from the group consisting of an N-alkylpyrrolidone, a lower alkylene carbonate and an aromatic alcohol;

(C) from 0.1–50 wt % of a lower alcohol or a lower polyol;

(D) from 0.01–10 wt % of an alkaline ingredient;

(E) from 0.1–20 wt % of a thickener; and (F)

at least one cosmetic ingredient selected from the group consisting of nonionic surfactants, amphiphatic ingredients, paraffin oils, lanoline, higher alcohols, silicone oils, bactericides, hair-growing and hair-nourishing agents, preservatives, antidandruff agents, aerosolizing agent and perfumes, and subsequently rinsing the hair thereby removing hair dye from the hair by dissolution of the dye from the hair without bleaching the hair which decomposes melanin contained in the hair.

\* \* \* \* \*